US012774266B2

(12) United States Patent
Shin et al.

(10) Patent No.: US 12,774,266 B2
(45) Date of Patent: Oct. 27, 2026

(54) RECOVERY METHOD AND RECOVERY APPARATUS OF NITRILE-BASED MONOMER

(71) Applicant: LG CHEM, LTD., Seoul (KR)

(72) Inventors: Sang Cheol Shin, Daejeon (KR); Jun Seok Ko, Daejeon (KR); Yong Heon Cho, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1086 days.

(21) Appl. No.: 17/628,717

(22) PCT Filed: Jul. 9, 2021

(86) PCT No.: PCT/KR2021/008780
§ 371 (c)(1),
(2) Date: Jan. 20, 2022

(87) PCT Pub. No.: WO2022/055104
PCT Pub. Date: Mar. 17, 2022

(65) Prior Publication Data
US 2022/0348536 A1 Nov. 3, 2022

(30) Foreign Application Priority Data
Sep. 11, 2020 (KR) ........................ 10-2020-0116811

(51) Int. Cl.
*C07C 253/34* (2006.01)
*C07C 253/02* (2006.01)

(52) U.S. Cl.
CPC .......... *C07C 253/34* (2013.01); *C07C 253/02* (2013.01)

(58) Field of Classification Search
CPC ... C07C 253/34; C07C 253/02; C07C 253/32; C07C 255/08; B01D 3/009; B01D 3/143
See application file for complete search history.

(56) References Cited

U.S. PATENT DOCUMENTS

| | | | |
|---|---|---|---|
| 3,954,910 A | 5/1976 | Kropp et al. | |
| 4,434,029 A | 2/1984 | Kurihara et al. | |
| 4,599,145 A * | 7/1986 | Kawakami | C07C 253/34 203/99 |
| 2005/0187401 A1 * | 8/2005 | Godbole | C07C 253/34 558/463 |

FOREIGN PATENT DOCUMENTS

| | | | |
|---|---|---|---|
| CN | 104922923 | A | 9/2015 |
| CN | 109529554 | A | 3/2019 |
| JP | 2003-292528 | A | 10/2003 |
| KR | 10-1985-0001603 | | 10/1985 |
| KR | 10-1992-0001320 | | 2/1992 |
| KR | 10-2001-0071471 | A | 7/2001 |
| KR | 10-2001-0104729 | A | 11/2001 |
| KR | 10-2003-0029619 | A | 4/2003 |
| KR | 10-0874030 | B1 | 12/2008 |
| KR | 10-2010-0086504 | A | 7/2010 |
| KR | 10-1701506 | B1 | 2/2017 |
| KR | 10-1838815 | B1 | 3/2018 |
| TW | 201940566 | A | 10/2019 |
| WO | 2012/090691 | A1 | 7/2012 |
| WO | 2019181697 | A1 | 9/2019 |

OTHER PUBLICATIONS

Office Action (with partial translation) dated Jun. 29, 2023, issued in corresponding Chinese Patent Application No. 202180004612.6.
International Search Report and Written Opinion issued in corresponding International Patent Application No. PCT/ KR2021/ 008780, dated Oct. 18, 2021.
Extended European Search Report dated Aug. 18, 2022, issued in corresponding European Patent Application No. 21836310.9.

* cited by examiner

*Primary Examiner* — Fereydoun G Sajjadi
*Assistant Examiner* — Anna Grace Kuckla
(74) *Attorney, Agent, or Firm* — Morgan, Lewis & Bockius LLP

(57) ABSTRACT

Disclosed is a recovery method of a nitrile-based monomer including: supplying a feed stream including a nitrile-based monomer, a nitrogen compound, and water to a first distillation tower to separate the stream into a lower discharge stream and an upper discharge stream; condensing the upper discharge stream of the first distillation tower and supplying the condensed stream to a decanter to separate the stream into a water layer and an organic layer; supplying an organic layer stream discharged from the decanter to a second distillation tower to separate the stream into a lower discharge stream and an upper discharge stream; and splitting a part of the upper discharge stream from the second distillation tower and refluxing the split stream to the second distillation tower.

7 Claims, 2 Drawing Sheets

【FIG. 1】
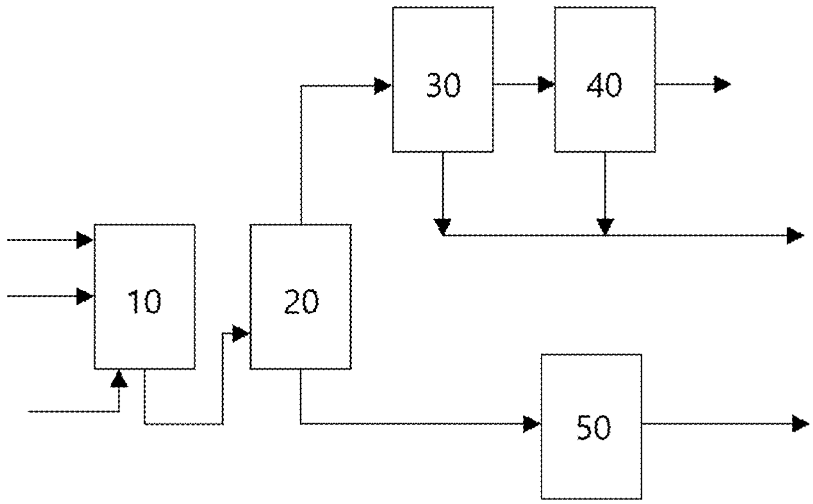
【FIG. 2】
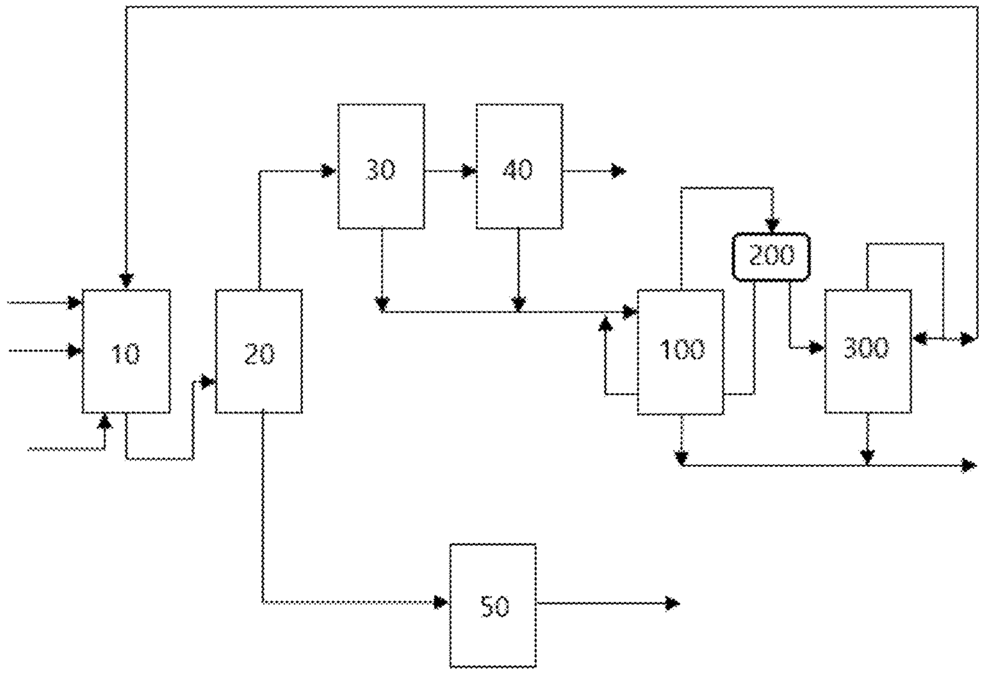

【FIG. 3】
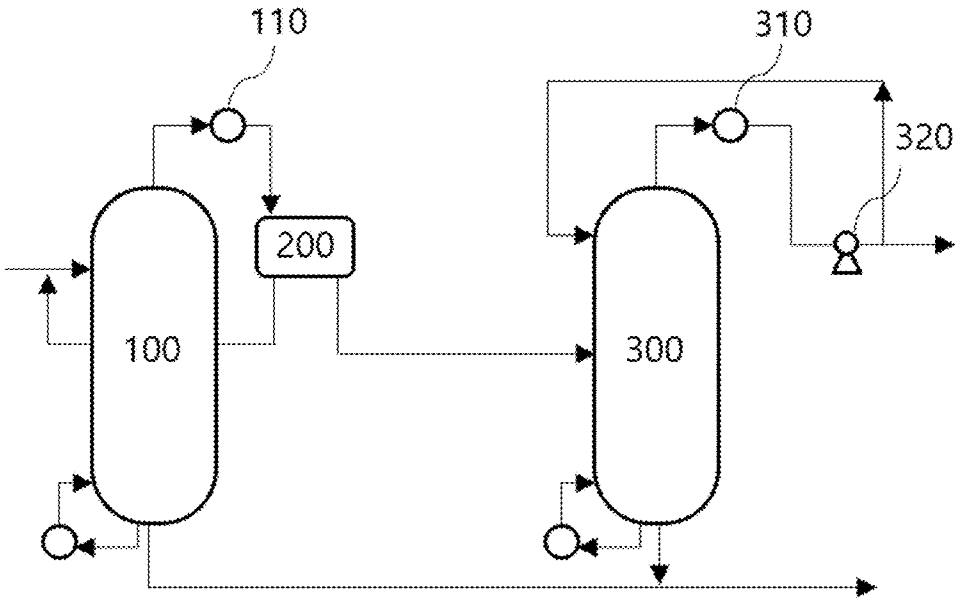
【FIG. 4】
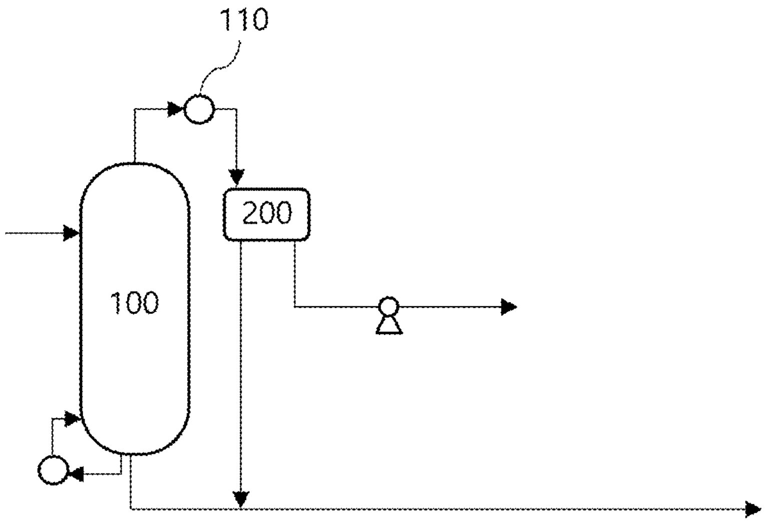

RECOVERY METHOD AND RECOVERY APPARATUS OF NITRILE-BASED MONOMER

CROSS-REFERENCE TO RELATED APPLICATIONS

The present application claims the benefit of priority to Korean Patent Application No. 10-2020-0116811, filed on Sep. 11, 2020, the entire contents of which are incorporated herein as a part of the specification.

TECHNICAL FIELD

The present invention relates to a recovery method and a recovery apparatus of a nitrile-based monomer, and more particularly, to a method of recovering a nitrile-based monomer from a recovery solution from a polymerization reaction including a nitrile-based monomer and a nitrogen compound and an apparatus for recovering a nitrile-based monomer.

BACKGROUND ART

In general, in a process of producing nitrile butadiene rubber latex (NBL), after a polymerization reaction of a nitrile-based monomer and butadiene, a pH adjusting agent is introduced to an aqueous polymer solution to adjust the pH. In this process, in a pH-adjusted aqueous polymer solution, nitrogen compounds containing nitrogen, such as acetonitrile, 2-methyl-2-propenenitrile, propionitrile, trans-crotononitrile, hydrogen cyanide, and oxazole are produced as by-products, as well as an acrylonitrile-butadiene (NB) copolymer and unreacted monomers.

Thereafter, the pH-adjusted aqueous polymer solution is supplied to a stripper and stripped under vacuum, thereby stripping the unreacted monomers and the nitrogen compounds in a gas state from an upper portion of the stripper, discharging an acrylonitrile-butadiene copolymer and water from a lower portion of the stripper, and then producing a final NBL product by a productization process of the lower discharge stream.

Meanwhile, from the gas stripped from the upper portion of the stripper, unreacted butadiene is separated by condensation and compression processes and the residue is recovered as a recovery solution, and since in the recovery solution, an unreacted nitrile-based monomer and nitrogen compounds are included, when the recovery solution is reused in the process, a problem of discoloration and odor (bad smell) occurrence arises in an NBL product, resulting in manufacture of an abnormal product.

Therefore, a large amount of the recovery solution is not reused in the process and should be all discharged as wastewater, and in this case, raw materials such as the unreacted nitrile-based monomer are lost, and also a further treatment of a nitrogen compound is needed for satisfying legal standards for wastewater discharge due to a high content of nitrogen compounds in wastewater. For this reason, a load on a wastewater treatment facility is increased and there is currently a difficulty in corresponding to reinforcing environmental regulations.

DISCLOSURE

Technical Problem

In order to solve the problems mentioned in Background Art, an object of the present invention is to purify a recovery solution from a polymerization reaction including a nitrile-based monomer and a nitrogen compound to recover the nitrile-based monomer in high purity and to lower a content of the nitrogen compound in the recovery solution discharged as wastewater to decrease a load on a wastewater treatment facility.

Technical Solution

In one general aspect, a recovery method of a nitrile-based monomer includes: supplying a feed stream including a nitrile-based monomer, a nitrogen compound, and water to a first distillation tower to separate the stream into a lower discharge stream including water and an upper discharge stream including the nitrile-based monomer, the nitrogen compound, and water (S10); condensing the upper discharge stream from the first distillation tower and supplying the condensed stream to a decanter to separate the stream into a water layer and an organic layer including the nitrile-based monomer and the nitrogen compound (S20); supplying an organic layer stream discharged from the decanter to a second distillation tower to separate the stream into a lower discharge stream including the nitrogen compound and an upper discharge stream including the nitrile-based monomer and the nitrogen compound (S30); and splitting a part of the upper discharge stream from the second distillation tower and refluxing the split stream to the second distillation tower (S40). In another general aspect, a recovery apparatus of a nitrile-based monomer includes: a first distillation tower which is supplied with a feed stream including a nitrile-based monomer, a nitrogen compound, and water and discharges a lower discharge stream including water and an upper discharge stream including the nitrile-based monomer, the nitrogen compound, and water; a first condenser which condenses the upper discharge stream from the first distillation tower; a decanter which is supplied with a discharge stream from the first condenser and separates the stream into a water layer and an organic layer including the nitrile-based monomer and the nitrogen compound; a second distillation tower which is supplied with the organic layer stream discharged from the decanter and discharges a lower discharge stream including the nitrogen compound and an upper discharge stream including the nitrile-based monomer and the nitrogen compound; a second condenser which condenses the upper discharge stream from the second distillation tower; and a pump which splits a part of the upper discharge stream from the second distillation tower and refluxes the split stream to the second distillation tower.

Advantageous Effects

Using the recovery method and the recovery apparatus of a nitrile-based monomer according to the present invention, a recovery solution from a polymerization reaction including a nitrile-based monomer and a nitrogen compound may be purified to recover the nitrile-based monomer in high purity and a content of the nitrogen compound in the recovery solution discharged as wastewater may be lowered to decrease a load on a wastewater treatment facility.

DESCRIPTION OF DRAWINGS

FIG. 1 is a process flow diagram showing a conventional flow of wastewater produced from a polymerization reaction of a nitrile-based monomer and a conjugated diene-based monomer.

FIG. 2 is a process flow diagram showing a recovery method of a nitrile-based monomer from wastewater produced from a polymerization reaction of a nitrile-based monomer and a conjugated diene-based monomer, according to an exemplary embodiment of the present invention.

FIG. 3 is a process flow diagram showing a recovery method of a nitrile-based monomer according to an exemplary embodiment of the present invention in detail.

FIG. 4 is a process flow diagram showing a recovery method of a nitrile-based monomer according to the Comparative Example.

BEST MODE

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "upper portion" means a portion corresponding to a height at or above 50% of a total height of an apparatus in a container and the term "lower portion" means a portion corresponding to a height less than 50% of a total height of an apparatus in a container or an apparatus.

The term "stream" in the present invention may refer to a fluid flow in a process, or may refer to a fluid itself flowing in a pipe. Specifically, the "stream" may refer to both a fluid itself flowing in a pipe connecting each device and a fluid flow. In addition, the fluid may refer to a gas or a liquid.

Hereinafter, the present invention will be described in more detail referring to the following FIGS. 1 to 4, for better understanding of the present invention.

According to the present invention, a recovery method of a nitrile-based monomer is provided. The recovery method of a nitrile-based monomer may include: supplying a feed stream including a nitrile-based monomer, a nitrogen compound, and water to a first distillation tower 100 to separate the stream into a lower discharge stream including water and an upper discharge stream including the nitrile-based monomer, the nitrogen compound, and water (S10); condensing the upper discharge stream of the first distillation tower 100 and supplying the condensed stream to a decanter 200 to separate the stream into a water layer and an organic layer including the nitrile-based monomer and the nitrogen compound (S20); supplying an organic layer stream discharged from the decanter 200 to a second distillation tower 300 to separate the stream into a lower discharge stream including the nitrogen compound and an upper discharge stream including the nitrile-based monomer and the nitrogen compound (S30); and splitting a part of the upper discharge stream from the second distillation tower 300 and refluxing the split stream to the second distillation tower 300 (S40).

According to an exemplary embodiment of the present invention, the feed stream may be discharged from a reactor 10 in which a nitrile-based monomer and a conjugated diene-based monomer are polymerized.

As a specific example, the feed stream may be produced after recovering the conjugated diene-based monomer and a nitrile-based monomer-conjugated diene-based monomer copolymer from a discharge stream from the reactor 10 including the nitrile-based monomer, the conjugated diene-based monomer, a nitrogen compound, water, and the nitrile-based monomer-conjugated diene-based monomer copolymer.

As a more specific example, the feed stream may be a mixed stream formed by mixing lower discharge streams from each of a condensation system 30 and a compressor 40, discharged from a polymerization process of the nitrile-based monomer-conjugated diene-based monomer copolymer described later. Hereinafter, referring to FIG. 2, the polymerization process of the nitrile-based monomer-conjugated diene-based monomer copolymer will be described in detail.

The polymerization process of the nitrile-based monomer-conjugated diene-based monomer copolymer may include: supplying a nitrile-based monomer, a conjugated diene-based monomer, and an additive to a reactor 10 to obtain an aqueous polymer solution (S1); supplying the aqueous polymer solution to a stripper 20 to separate a gaseous upper discharge stream including unreacted monomers, water, and a nitrogen compound and a lower discharge stream including the nitrile-based monomer-conjugated diene-based monomer copolymer and water from the stripper 20 (S2); and sequentially passing the upper discharge stream from the stripper 20 through a condensation system 30 and a compressor 40 to be separated into a lower discharge stream from each of the condensation system 30 and the compressor 40, including the nitrile-based monomer, the nitrogen compound, and water and an upper discharge stream from the compressor 40, including a gaseous conjugated diene-based monomer (S3).

Here, in (S2), the lower discharge stream from the stripper 20 is passed through a productization process unit to obtain the nitrile-based monomer-conjugated diene-based monomer copolymer in high purity.

In addition, in (S3), the upper discharge stream from the compressor 40 including the conjugated diene-based monomer is resupplied to the reactor 10, so that the conjugated diene-based monomer may be reused as a raw material of a polymerization reaction.

In addition, in (S3), the lower discharge streams from each of the condensation system 30 and the compressor 40, including the nitrile-based monomer, the nitrogen compound, and water may be mixed and supplied to a first distillation tower 100 as the feed stream of the recovery method of a nitrile-based monomer according to the present invention, as described above.

According to an exemplary embodiment of the present invention, the stripper 20 may be an apparatus to perform a stripping process, and the stripping may refer to separation and removal of gas dissolved in a liquid. For example, the stripping may be performed by a method such as direct contact, heating, and pressurization by steam, inert gas, air, and the like, and the stripping in the present specification may be used in the same meaning as dissipation.

According to an exemplary embodiment of the present invention, the additive supplied to the reactor 10 in (S1) may be added for securing easy polymerization. If necessary, the process may be performed by including an additive such as an initiator, a molecular weight adjusting agent, an activator, an oxidation/reduction catalyst activator, a chelating agent, a dispersant, a deoxidizer, a particle diameter adjusting agent, a pH adjusting agent, an anti-aging agent, an antioxidant, a defoamer, and an oxygen scavenger. As a specific example, the additive may be an additive including nitrogen, and as a more specific example, the additive may be ammonia ($NH_3$) which is a pH adjusting agent.

According to an exemplary embodiment of the present invention, the nitrile-based monomer includes one or more selected from the group consisting of acrylonitrile, methacrylonitrile, fumaronitrile, α-chloronitrile, and α-cyanoethylacrylonitrile, but is not limited thereto. As a specific example, the nitrile-based monomer may be acrylonitrile, and in this case, the nitrile-based monomer may be easily obtained in high purity from the upper discharge stream from the second distillation tower 300 described later.

According to an exemplary embodiment of the present invention, the conjugated diene-based monomer may include one or more selected from the group consisting of 1,3-butadiene, 1,4-butadiene, 2,3-dimethyl-1,3-butadiene, 2-ethyl-1,3-butadiene, 1,3-pentadiene, piperylene, 3-butyl-1,3-octadiene, 2-phenyl-1,3-butadiene, and isoprene, but is not limited thereto. As a specific example, the conjugated diene-based monomer may be 1,3-butadiene or 1,4-butadiene, and thus, the copolymer produced by the polymerization reaction may be acrylonitrile-butadiene copolymer, that is, nitrile butadiene rubber latex (NBL).

Conventionally, after the polymerization reaction of the nitrile-based monomer and the conjugated diene monomer, an additive was introduced to the aqueous polymer solution for improving processability of the nitrile-based monomer-conjugated diene-based monomer copolymer. In this process, in the produced aqueous polymer solution, a nitrogen compound such as acetonitrile (ACN), 2-methyl-2-propenenitrile (MPN), propionitrile (PRN), trans-crotononitrile (T-CRN), hydrogen cyanide (HCN), and oxazole (OZ) is are produced as by-products, as well as the nitrile-based monomer-conjugated diene-based monomer copolymer and unreacted monomers.

As a specific example, the nitrogen compound may be mainly derived from a nitrile-based monomer, and also, may be further produced as by-products from a nitrogen-containing additive, for example, ammonia ($NH_3$) or impurities contained in the nitrile-based monomer before a polymerization reaction, for example, hydrogen cyanide (HCN) and the like.

The nitrogen compound is included in the lower discharge streams from each of the condensation system 30 and the compressor 40 in (S3) described above, together with the nitrile-based monomer.

Here, when a mixed stream in which the lower discharge streams from each of the condensation system 30 and the compressor 40 are mixed is resupplied to the reactor 10 for reusing the nitrile-based monomer as the raw materials of the polymerization reaction, the nitrile-based monomer-conjugated diene-based monomer copolymer discharged from a productization process unit 50 through which the mixed stream is passed includes a large amount of the nitrogen compound and causes discoloration and odor (bad smell), and thus, an abnormal product is produced.

For this reason, the lower discharge streams from the condensation system 30 and the compressor 40 are not reused in the process and all discharged as wastewater, but in this case, the raw materials such as an unreacted nitrile-based monomer are lost, and a further treatment of a nitrogen-containing component is needed for satisfying legal standards for wastewater discharge due to a high content of nitrogen compound in wastewater, and thus, a load on a wastewater treatment facility is increased.

Accordingly, in the present invention, a mixed stream of the lower discharge streams from each of the condensation system 30 and the compressor 40 is supplied to a feed stream of the recovery method of a nitrile-based monomer according to the present invention, thereby recovering the nitrile-based monomer in high purity, and lowering a content of nitrogen-containing components in the stream discharged as wastewater to decrease the load on the wastewater treatment facility.

According to an exemplary embodiment of the present invention, the recovery method of a nitrile-based monomer according to the present invention may include supplying a feed stream including a nitrile-based monomer, a nitrogen compound, and water to a first distillation tower 100 to separate the stream into a lower discharge stream including water and an upper discharge stream including the nitrile-based monomer, the nitrogen compound, and water (S10).

As described above, the feed stream may be a discharge stream from a reactor 10 including the nitrile-based monomer, the nitrogen compound, and water remaining after recovering the conjugated diene-based monomer and the nitrile-based monomer-conjugated diene-based monomer copolymer from the discharge stream from the reactor 10 in which the nitrile-based monomer and the conjugated diene-based monomer are polymerized.

Here, the nitrogen compound, which is a component produced as a by-product from the nitrile-based monomer and an additive containing nitrogen, may include one or more selected from the group consisting of acetonitrile, 2-methyl-2-propenenitrile, propionitrile, trans-crotononitrile, hydrogen cyanide, and oxazole.

As a specific example, the nitrogen compound may include a material having a higher boiling point than the nitrile-based monomer. As a more specific example, the nitrogen compound may include acetonitrile, 2-methyl-2-propenenitrile, propionitrile, and trans-crotononitrile, and in this case, the nitrile-based monomer may be easily obtained in high purity from an upper discharge stream from a succeeding second distillation tower 300.

In (S10), as described above, the feed stream including the nitrile-based monomer, the nitrogen compound, and water is supplied to the first distillation tower 100 to discharge water having a higher boiling point than the nitrile-based monomer to a lower portion of the first distillation tower 100 and to discharge the nitrogen compound and the nitrile-based monomer having a lower boiling point than water to an upper portion of the first distillation tower 100.

Meanwhile, in this step, a part of the nitrogen compound having a higher boiling point than the nitrile-based monomer and a part of the nitrogen compound having a higher boiling point than water may be discharged with water to the lower portion of the first distillation tower 100. For example, the part of the nitrogen compound having a higher boiling point than the nitrile-based monomer may include acetonitrile, 2-methyl-2-propenenitrile, and propionitrile, and the part of the nitrogen compound having a higher boiling point than water may include trans-crotononitrile.

According to an exemplary embodiment of the present invention, the feed stream may be supplied to a plate at 50% or less, 1% to 30%, or 1% to 10% of the theoretical plate number of the first distillation tower 100. For example, when the theoretical plate number of the first distillation tower 100 is 100, the top plate may be the first plate and the bottom plate may be 100th plate, and the plate at 50% or less of the theoretical plate number may mean first to 50th plates of the first distillation tower 100. The feed stream is supplied to the plate in the above range of the first distillation tower 100, thereby improving a contact efficiency of a gaseous component vaporized in the lower portion of the first distillation tower 100 and the liquid component of the feed stream to easily discharge the nitrile-based monomer having a low boiling point and the nitrogen compound to the upper portion of the first distillation tower 100, and thus, a content of the nitrile-based monomer lost in the lower portion of the first distillation tower 100 may be decreased and a content of the nitrile-based monomer in the upper discharge stream from the first distillation tower 100 may be increased.

According to an exemplary embodiment of the present invention, the recovery method of a nitrile-based monomer according to the present invention may include condensing the upper discharge stream from the first distillation tower 100 and supplying the condensed stream to a decanter (200) to separate the stream into a water layer and an organic layer including the nitrile-based monomer and the nitrogen compound (S20).

(S20) may be a step of passing the upper discharge stream from the first distillation tower 100 including the nitrile-based monomer and the nitrogen compound through a first condenser 110 to condense the stream and then supplying the condensed stream to a decanter 200 to separate the stream into a water layer and an organic layer including the nitrile-based monomer and the nitrogen compound.

Thereafter, the water layer stream discharged from the decanter 200 is mixed with the feed stream of (S10) to form a mixed stream, and the mixed stream may be resupplied to the first distillation tower 100. As such, the water layer stream is mixed with the feed stream and resupplied to the first distillation tower 100, thereby improving a purification efficiency of the nitrile-based monomer and the nitrogen compound to decrease amounts of the nitrile-based monomer and the nitrogen compound discharged as wastewater, and increasing the content of water in the feed stream supplied to the first distillation tower 100 to easily separate the nitrogen compound and the nitrile-based monomer having a lower boiling point than water in the lower portion of the first distillation tower 100.

In addition, the organic layer and the water layer are separated and only the organic layer stream is supplied to the second distillation tower 300, thereby decreasing the amount of water supplied to the second distillation tower 300 to obtain the nitrile-based monomer in high purity from the second distillation tower 300.

According to an exemplary embodiment of the present invention, the recovery method of a nitrile-based monomer according to the present invention may include supplying the organic layer stream discharged from the decanter 200 to the second distillation tower 300 to separate the stream into a lower discharge stream including the nitrogen compound and an upper discharge stream including the nitrile-based monomer and the nitrogen compound (S30).

(S30) may be a step in which the organic layer stream including the nitrile-based monomer and the nitrogen compound is supplied to the second distillation tower 300 to discharge the nitrogen compound having a higher boiling point than the nitrile-based monomer to a lower portion of the second distillation tower 300 and the nitrile-based monomer having a lower boiling point than the nitrogen compound to an upper portion of the second distillation tower 300.

Meanwhile, in this step, the nitrogen compound having a lower boiling point than the nitrile-based monomer may be also discharged with the nitrile-based monomer to the upper portion of the second distillation tower 300. For example, the nitrogen compound having a lower boiling point than the nitrile-based monomer may include hydrogen cyanide and oxazole.

According to an exemplary embodiment of the present invention, the organic layer stream may be supplied to a plate at 40% to 60%, 45% to 55%, or 48% to 52% of the theoretical plate number of the second distillation tower 300. For example, when the theoretical plate number of the second distillation tower 300 is 100, the top plate may be the first plate and the bottom plate may be 100th plate, and the plate at 40% to 60% of the theoretical plate number may mean 40th to 60th plates of the first distillation tower 100. The organic layer stream is supplied to the plate in the above range of the second distillation tower 300, thereby recovering a high-purity nitrile-based monomer from the upper discharge stream from the second distillation tower 300.

According to an exemplary embodiment of the present invention, the recovery method of a nitrile-based monomer according to the present invention may include splitting a part of the upper discharge stream from the second distillation tower 300 and refluxing the split stream to the second distillation tower 300 (S40).

(S40) may be a step in which the upper discharge stream from the second distillation tower 300 including the nitrile-based monomer and the nitrogen compound having a lower boiling point than the nitrile-based monomer is discharged, and a part of the stream is split and refluxed to the second distillation tower 300.

Here, a ratio of a flow rate of the stream which is partly split from the upper discharge stream from the second distillation tower 300 and refluxed to the second distillation tower 300, relative to a total flow rate of the upper discharge stream from the second distillation tower 300 may be 0.50 to 0.80, 0.60 to 0.75, or 0.65 to 0.68.

When the flow rate ratio of the stream is 0.50 or more, a separation efficiency of the nitrile-based monomer and the nitrogen compound in the second distillation tower 300 is excellent, so that a high-purity nitrile-based monomer may be obtained from the upper portion of the second distillation tower 300, and when the flow rate ratio of the stream is 0.80 or less, an energy loss in the process is prevented and a higher capacity of a distillation tower, a pipe, a pump, and the like due to an unnecessary increase of the size (volume) of the entire apparatus is prevented, thereby preventing an increase in power consumption and an increase in separation efficiency hunting elements due to control instability.

For example, when the flow rate ratio of the stream is satisfied, the nitrile-based monomer is acrylonitrile, the conjugated diene-based monomer is butadiene, and an additive including nitrogen is used as an additive in the polymerization reaction of the nitrile-based monomer-conjugated diene-based monomer copolymer, the contents of the nitrogen compound derived from the additive and the nitrile-based monomer in the upper discharge stream from the second distillation tower 300 are decreased, thereby resupplying the high-purity nitrile-based monomer to the reactor 10, and thus, a discoloration and odor (bad smell) occurring problem of the nitrile-based monomer-conjugated diene-based monomer copolymer finally obtained in the productization process unit 500 is prevented to obtain an excellent high-purity product.

According to an exemplary embodiment of the present invention, a reflux stream of the second distillation tower 300 may be supplied to a plate at 50% or less, 1% to 25%, or 1% to 10% of the theoretical plate number of the second distillation tower 300. For example, when the theoretical plate number of the second distillation tower 300 is 100, the top plate may be the first plate and the bottom plate may be 100th plate, and the plate at 50% or less of the theoretical plate number may mean first to 50th plates of the second distillation tower 300. The feed stream is supplied to the plate in the above range of the second distillation tower 300, whereby a residence time in the second distillation tower 300 is increased to improve a material transfer efficiency by contact between a gaseous component vaporized and a liquid component liquefied from the reflux stream, so that a separation efficiency may be improved, and as a result, the content of the nitrile-based monomer lost in the lower portion of the second distillation tower 300 may be decreased and the content of the nitrile-based monomer in the upper discharge stream from the second distillation tower 300 may be increased.

According to an exemplary embodiment of the present invention, a temperature of the top plate of the first distillation tower 100 may be 94 to 100° C., 95 to 99° C., or 96 to 98° C., an operation pressure of the first distillation tower 100 may be 0.01 to 0.2 kg/cm$^2$G, 0.02 to 0.10 kg/cm$^2$G, or 0.04 to 0.06 kg/cm$^2$G, and within the range, a separation efficiency of the nitrogen compound and water having a higher boiling point than the nitrile-based monomer may be improved.

According to an exemplary embodiment of the present invention, a temperature of the bottom plate of the second distillation tower 300 may be 80 to 90° C., 82 to 88° C., or 84 to 86° C., an operation pressure of the second distillation tower 300 may be 0.1 to 0.7 kg/cm$^2$G, 0.2 to 0.5 kg/cm$^2$G, or 0.2 to 0.3 kg/cm$^2$G, and within the range, a separation efficiency of the nitrogen compound having a higher boiling point than the nitrile-based monomer may be improved.

According to an exemplary embodiment of the present invention, the upper discharge stream from the second distillation tower 300 including the nitrile-based monomer is resupplied to the rector 10 in which the nitrile-based monomer-conjugated diene-based monomer copolymer is polymerized to be reused as a raw material of the polymerization reaction.

The total content of the nitrile-based monomer included in the upper discharge stream from the second distillation tower 300 may be 97 wt % or more, 98 wt % or more, or 99.5 wt %, excluding water. In addition, the total content of the nitrogen compound included in the upper discharge stream from the second distillation tower 300 may be 0.5 wt % or less or 0.3 to 0.1 wt %, excluding water.

As such, when the nitrile-based monomer is separated by the recovery method according to the present invention, the purity of the finally recovered nitrile-based monomer may be increased and the content of the nitrogen compound included as a by-product may be significantly decreased.

According to an exemplary embodiment of the present invention, a recovery solution recovered from the lower discharge stream from the first distillation tower 100 and the lower discharge stream from the second distillation tower 300 may be treated as wastewater.

The content of the nitrogen compound included in the recovery solution treated as wastewater may be decreased by 75% or more, 85% or more, or 90% or more relative to the feed stream supplied to the first distillation tower 100 in (S10).

As such, when the nitrile-based monomer is separated by the recovery method according to the present invention, 85% or more of the content of the nitrogen in the recovery solution finally discharged and treated as wastewater (total N) is removed to decrease a load on a wastewater treatment facility.

According to the present invention, a recovery apparatus of a nitrile-based monomer is provided. The recovery apparatus of a nitrile-based monomer may include a first distillation tower 100, a first condenser 110, a decanter 200, a second distillation tower 300, a second condenser 310, and a pump 320, as shown in FIG. 3.

As a specific example, the recovery apparatus of a nitrile-based monomer may include: a first distillation tower 100 which is supplied with a feed stream including a nitrile-based monomer, a nitrogen compound, and water and discharges a lower discharge stream including water and an upper discharge stream including the nitrile-based monomer, the nitrogen compound, and water; a first condenser 110 which condenses the upper discharge stream from the first distillation tower 100; a decanter 200 which is supplied with a discharge stream from the first condenser 110 and separates the stream into a water layer and an organic layer including the nitrile-based monomer and the nitrogen compound; a second distillation tower 300 which is supplied with the organic layer stream discharged from the decanter 200 and discharges a lower discharge stream including the nitrogen compound and an upper discharge stream including the nitrile-based monomer and the nitrogen compound; a second condenser 310 which condenses the upper discharge stream from the second distillation tower 300; and a pump 320 which splits a part of the upper discharge stream from the second distillation tower 300 and refluxes the split stream to the second distillation tower 300.

According to an exemplary embodiment of the present invention, the recovery apparatus of a nitrile-based monomer according to the present invention may be an apparatus for performing the process according to the recovery method of a nitrile-based monomer described above.

According to an exemplary embodiment of the present invention, the recovery apparatus of a nitrile-based monomer according to the present invention may be provided with a pipe connecting among the first distillation tower 100, the first condenser 110, the decanter 200, the second distillation tower 300, the second condenser 310, and the pump 320, and in order to easily supply the lower discharge stream and the upper discharge stream of each constituent to the constituent of a succeeding apparatus, a pump (not shown) may be further provided on the pipe.

According to an exemplary embodiment of the present invention, in the recovery method and recovery apparatus of a nitrile-based monomer according to the present invention, a distillation tower (not shown), a condenser (not shown), a reboiler (not shown), a pump (not shown), a compressor (not shown), a mixer (not shown), a separator (not shown), and the like may be further installed, if necessary.

Hereinabove, the recovery method and the recovery apparatus of a nitrile-based monomer according to the present invention have been described and illustrated in the drawings, but the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for carrying out the recovery method and the recovery apparatus of a nitrile-based monomer according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES AND COMPARATIVE EXAMPLES

Comparative Example 1

As shown in the process flow diagram illustrated in FIG. 1, butadiene, acrylonitrile, and water were supplied to the reactor 10 and were polymerized in the presence of a catalyst to obtain an aqueous polymer solution after completing polymerization. Thereafter, ammonia was introduced as a pH adjusting agent to the aqueous polymer solution to adjust the pH to 10. At this time, the aqueous polymer solution after completing the pH adjustment included water, an acrylonitrile-butadiene copolymer, an unreacted monomer, and a nitrogen compound.

Thereafter, the aqueous polymer solution after completing the pH adjustment was supplied to the stripper and stripped under vacuum, thereby stripping the unreacted monomers (butadiene and acrylonitrile), water, and the nitrogen compound in a gaseous state from an upper portion of the stripper 20, and discharging the acrylonitrile-butadiene copolymer and water from a lower portion.

Thereafter, the lower discharge stream from the stripper 20 was introduced to the productization process unit 50 to obtain a nitrile butadiene rubber latex (NBL).

Thereafter, gas stripped from an upper portion of the stripper 20 was supplied to the condensation system 30 so that most acrylonitrile, water, and the nitrogen compound were condensed to be recovered as wastewater. In addition, uncondensed gas from the condensation system 30 was passed through the compressor 40 so that residual acrylonitrile, water, and nitrogen compound were condensed to be recovered as wastewater, and butadiene was separated in a gas state.

In the process, the purity of acrylonitrile, the content of the nitrogen compound, and the content of the nitrogen-containing component in the total wastewater (6.5 ton/hr, 3.5 kg/cm$^2$G) recovered from the discharge stream from the condensation system 30 and the compressor 40 are shown in the following Table 1.

Comparative Example 2

As shown in the process flow diagram illustrated in FIG. 4, the wastewater recovered in Comparative Example 1 was supplied to the top plate (1st plate) of the first distillation tower 100 having a total of 5 theoretical plates, and a lower discharge stream including a large amount of water, the nitrogen compound, and a part of acrylonitrile and an upper discharge stream including a large amount of acrylonitrile and nitrogen compound and a part of water were separated.

Thereafter, the upper discharge stream from the first distillation tower 100 was passed through the first condenser 110 to be condensed to 40° C. and supplied to the decanter 200 to be separated into a water layer and an organic layer including acrylonitrile and the nitrogen compound, and the water layer stream discharged from the decanter 200 was mixed with the lower discharge stream from the first distillation tower 100 and recovered as wastewater.

Thereafter, the organic layer stream discharged from the decanter 200 was resupplied to the reactor 10 for NBL polymerization and then NBL was obtained by the productization process unit 50.

In the process, the operation condition of the first distillation tower 100, the content of the nitrogen-containing component in the recovered wastewater, the purity of acrylonitrile in the organic layer stream, and the content of the nitrogen compound are shown in the following Table 1.

Comparative Example 3

The process was simulated in the same manner as in Comparative Example 2, except that operation was performed by changing the tower top temperature to 101° C.

In the process, the operation conditions of the first distillation tower 100, the content of the nitrogen-containing component in the recovered wastewater, the purity of acrylonitrile in the organic layer stream, and the content of the nitrogen compound are shown in the following Table 1.

Example 1

As shown in the process flow diagram illustrated in FIG. 3, the total wastewater recovered in Comparative Example 1 was supplied to the top plate (1st plate) of the first distillation tower 100 having a total of 5 theoretical plates, and a lower discharge stream including a large amount of water, the nitrogen compound, and a part of acrylonitrile and an upper discharge stream including a large amount of acrylonitrile and nitrogen compound and a part of water were separated.

Thereafter, the upper discharge stream from the first distillation tower 100 was passed through the first condenser 110 to be condensed to 40° C. and supplied to the decanter 200 to be separated into a water layer and an organic layer including acrylonitrile and the nitrogen compound, and the water layer stream discharged from the decanter 200 was mixed with the feed stream supplied to the first distillation tower 100 and resupplied to the first distillation tower 100.

Thereafter, the organic layer stream discharged from the decanter 200 was supplied to a middle plate (6th plate) of the second distillation tower 300 having a total of 11 theoretical plates to be separated into the lower discharge stream including the nitrogen compound and the upper discharge stream including acrylonitrile and the nitrogen compound.

Thereafter, the upper discharge stream from the second distillation tower 300 was passed through the second condenser 310 to be condensed to 40° C., a part of the stream was split and refluxed to the top plate (1st plate) of the second distillation tower, and the unrefluxed remaining stream was resupplied to the reactor 10, as shown in FIG. 2.

Here, a ratio of a flow rate of the stream which is partly split from the upper discharge stream from the second distillation tower 300 and refluxed to the second distillation tower 300, relative to a total flow rate of the upper discharge stream from the second distillation tower 300, was 0.67 (rounded off to two decimal places).

Thereafter, the lower discharge stream from the first distillation tower 100 and the lower discharge stream from the second distillation tower 300 were mixed and treated as wastewater, and NBL was obtained by the productization process unit 50.

In the process, the operation conditions of the first distillation tower 100 and the second distillation tower 300, the content of the nitrogen-containing component in the recovered wastewater, the purity of acrylonitrile in the upper discharge stream from the second distillation tower 300, and the content of the nitrogen compound are shown in the following Table 1.

Example 2

The process was simulated in the same manner as in Example 1, except that reflux was performed so that a ratio of a flow rate of the stream which is partly split from the upper discharge stream from the second distillation tower 300 and refluxed to the second distillation tower 300, relative to a total flow rate of the upper discharge stream from the second distillation tower 300 was 0.2 (rounded off to two decimal places).

Example 3

The process was simulated in the same manner as in Example 1, except that reflux was performed so that a ratio of a flow rate of the stream which is partly split from the upper discharge stream from the second distillation tower 300 and refluxed to the second distillation tower 300, relative to a total flow rate of the upper discharge stream from the second distillation tower 300 was 0.86 (rounded off to two decimal places).

was supplied to one first distillation tower 100 according to Comparative Example 2 to recover unreacted acrylonitrile, the content (purity) of acrylonitrile in the recovered organic layer stream was 97.5 wt % (dry), and the total concentration of the nitrogen-containing component in wastewater was 2397 ppm, which shows a removal rate of 84.5 wt % relative to wastewater supplied to the first distillation tower 100. However, in the organic layer stream recovered in Comparative Example 2, the content of acetonitrile (ACN), 2-methyl-2-propenenitrile (MPN), propionitrile (PRN), and trans-crotononitrile (T-CRN) having a higher boiling point than acrylonitrile and containing nitrogen was 1.53 wt % relative to acrylonitrile, which shows a removal rate of 15 wt % relative to wastewater supplied to the first distillation tower 100. As such, when the organic layer stream including a large amount of the nitrogen compound was resupplied to the reactor 10 for NBL polymerization and reused, a prob-

TABLE 1

| Classification | First distillation tower 100 | | | Second distillation tower 300 | | | * Discharge stream from second distillation tower | | Content of nitrogen-containing component in wastewater (weight ppm) |
|---|---|---|---|---|---|---|---|---|---|
| | Number of plates | Tower top temperature (° C.) | Pressure (kg/cm²G) | Number of plates | Tower bottom temperature (° C.) | Pressure (kg/cm²G) | * Content of AN (wt %) | Content of nitrogen compound (wt %) | |
| Example 1 | 5 | 97 | 0.05 | 11 | 85 | 0.2 | 99.5 | 0.36 (removed by 79 wt %) | 1973 (decreased by 87.3%) |
| Example 2 | 5 | 97 | 0.05 | 11 | 84 | 0.2 | 99.2 | 0.70 (removed by 75.5 wt %) | 3846 (decreased by 75.2 wt %) |
| Example 3 | 5 | 97 | 0.05 | 11 | 87 | 0.2 | 99.5 | 0.39 (removed by 77.2 wt %) | 1005 (decreased by 93.5%) |
| Comparative Example 1 | | | | — | | | 97.5 | 1.51 | 15517 |
| Comparative Example 2 | 5 | 97 | 0.05 | | — | | 97.5 | 1.53 (removed by 15 wt %) | 2397 (decreased by 84.5%) |
| Comparative Example 3 | 5 | 101 | 0.05 | | — | | 98.1 | 1.51 (removed by 1 wt %) | 119 (decreased by 99.2%) |

* AN: acrylonitrile

* Discharge stream from second distillation tower: total wastewater recovered from the discharge stream from the condensation system 30 and the compressor 40 in Comparative Example 1, and an organic layer stream in Comparative Examples 2 and 3.

Referring to Table 1, the content (purity) of acrylonitrile in wastewater recovered from the conventional NBL production process (Comparative Example 1) was 97.5 wt % (1.5 wt % (wet)), the content of acetonitrile (ACN), 2-methyl-2-propenenitrile (MPN), propionitrile (PRN), and trans-crotononitrile (T-CRN) having a higher boiling point than acrylonitrile and including nitrogen was 1.51 wt % with respect to acrylonitrile, and the total concentration of the nitrogen-containing component in wastewater was 15517 ppm. In this case, a large amount of impurities other than acrylonitrile was included in the wastewater even excluding water, and thus, when the wastewater was resupplied to the reactor 10 for NBL polymerization and reused, the product was adversely affected by the problem of discoloration and odor (bad smell) occurrence of the NBL product obtained by the productization process unit 50. In addition, since the content of the nitrogen-containing component in wastewater which was to be treated for complying with environmental regulations for wastewater discharge was high, the load on the wastewater treatment facility was large.

Meanwhile, when wastewater recovered in the conventional NBL production process (Comparative Example 1)

lem of discoloration and odor (bad smell) occurrence of the NBL product obtained by the productization process unit 50 arose.

In addition, in Comparative Example 3 in which operation was performed so that the tower top temperature of the first distillation tower 100 was changed from 97° C. in Comparative Example 2 to 101° C., the content (purity) of acrylonitrile in the recovered organic layer stream was 98.2 wt %, and the total concentration of the nitrogen-containing component in wastewater was 119 ppm, which shows a removal rate of 99.2 wt % relative to wastewater supplied to the first distillation tower 100. However, in the organic layer stream recovered in Comparative Example 3, the content of acetonitrile (ACN), 2-methyl-2-propenenitrile (MPN), propionitrile (PRN), and trans-crotononitrile (T-CRN) having a higher boiling point than acrylonitrile and containing nitrogen was 1.51 wt % relative to acrylonitrile, and thus, it was confirmed that the nitrogen compound was hardly removed relative to wastewater supplied to the first distillation tower 100. As such, when the organic layer stream including a large amount of the nitrogen compound was resupplied to the reactor 10 for NBL polymerization and reused, a problem of discoloration and odor (bad smell) occurrence of the NBL product obtained by the productization process unit 50 arose.

In order to solve the problems of the Comparative Examples, in Example 1 in which unreacted acrylonitrile was recovered from wastewater recovered in the conventional NBL production process (Comparative Example 1) using continuous two distillation towers, the content (purity) of acrylonitrile in the recovered upper discharge stream from the second distillation tower 300 was 99.5 wt % (dry), the content of acetonitrile (ACN), 2-methyl-2-propenenitrile (MPN), propionitrile (PRN), and trans-crotononitrile (T-CRN) having a higher boiling point than acrylonitrile and containing nitrogen was 0.36 wt % relative to acrylonitrile, which shows a removal rate of 79 wt % relative to wastewater supplied to the first distillation tower 100, a significantly higher removal rate of the nitrogen compound as compared with the Comparative Examples. As such, when the upper discharge stream from the second distillation tower 300 including a small amount of the nitrogen compound was resupplied to the reactor 10 for NBL polymerization and reused, a problem of discoloration and odor (bad smell) occurrence of the NBL product obtained by a productization process unit 50 did not arise. In addition, the total concentration of the nitrogen-containing component in the recovered wastewater was 1973 ppm, which shows a removal rate of 87.3 wt % relative to wastewater supplied to the first distillation tower 100, and thus, it was confirmed that the load on the wastewater treatment facility may be decreased.

The invention claimed is:

1. A recovery method of a nitrile-based monomer, the method comprising:

supplying a feed stream comprising a nitrile-based monomer, a nitrogen compound, and water to a first distillation tower to separate the stream into a lower discharge stream comprising water and an upper discharge stream comprising the nitrile-based monomer, the nitrogen compound, and water (S10);

condensing the upper discharge stream from the first distillation tower and supplying the condensed stream to a decanter to separate the stream into a water layer and an organic layer comprising the nitrile-based monomer and the nitrogen compound (S20);

supplying an organic layer stream discharged from the decanter to a second distillation tower to separate the stream into a lower discharge stream comprising the nitrogen compound and an upper discharge stream comprising the nitrile-based monomer and the nitrogen compound (S30); and splitting a part of the upper discharge stream from the second distillation tower and refluxing the split stream to the second distillation tower (S40), wherein the feed stream is discharged from a reactor in which the nitrile-based monomer and a conjugated diene-based monomer are polymerized, wherein in (S40), a ratio of a flow rate of a stream which is partly split from the upper discharge stream from the second distillation tower and refluxed to the second distillation tower relative to a total flow rate of the upper discharge stream from the second distillation tower is 0.5 to 0.8, and an unrefluxed remaining split stream of the upper discharge stream from the second distillation tower is resupplied to the reactor, wherein the split stream refluxed to the second distillation tower is supplied to a top plate of the second distillation tower, wherein the organic layer stream discharged from the decanter comprises the nitrile-based monomer and the nitrogen compound, and wherein the organic layer stream discharged from the decanter is directly supplied to the second distillation tower.

2. The recovery method of claim 1, wherein the nitrogen compound comprises one or more selected from the group consisting of acetonitrile, 2-methyl-2-propenenitrile, propionitrile, trans-crotononitrile, hydrogen cyanide, and oxazole.

3. The recovery method of claim 1, wherein the nitrogen compound comprises a material having a higher boiling point than the nitrile-based monomer.

4. The recovery method of claim 1, wherein the feed stream is produced after recovering the conjugated diene-based monomer and a nitrile-based monomer-conjugated diene-based monomer copolymer from a discharge stream from the reactor comprising the nitrile-based monomer, the conjugated diene-based monomer, a nitrogen compound, water, and the nitrile-based monomer-conjugated diene-based monomer copolymer.

5. The recovery method of claim 1, wherein a water layer stream discharged from the decanter is mixed with the feed stream and resupplied to the first distillation tower.

6. The recovery method of claim 1, wherein the feed stream is supplied to a plate at 50% or less of the theoretical plate number of the first distillation tower.

7. The recovery method of claim 1, wherein the organic layer stream is supplied to a plate at 40% to 60% of the theoretical plate number of the second distillation tower.

* * * * *